(12) United States Patent
Rajagopalan et al.

(10) Patent No.: US 7,303,926 B2
(45) Date of Patent: Dec. 4, 2007

(54) METHODS AND COMPOSITIONS FOR DUAL PHOTOTHERAPY

(75) Inventors: Raghavan Rajagopalan, Beechwood, OH (US); Samuel I. Achilefu, St. Louis, MO (US); Joseph E. Bugaj, St. Charles, MO (US); Richard B. Dorshow, St. Louis, MO (US)

(73) Assignee: Mallinckrodt, Inc, St. Louis, MO (US)

( * ) Notice: Subject to any disclaimer, the term of this patent is extended or adjusted under 35 U.S.C. 154(b) by 487 days.

(21) Appl. No.: 10/776,840

(22) Filed: Feb. 11, 2004

(65) Prior Publication Data
US 2004/0161430 A1    Aug. 19, 2004

Related U.S. Application Data

(62) Division of application No. 09/898,885, filed on Jul. 3, 2001, now abandoned.

(51) Int. Cl.
*G01N 33/533* (2006.01)
*G01N 21/76* (2006.01)
*A61K 39/00* (2006.01)

(52) U.S. Cl. ............... 436/546; 436/172; 436/800; 435/968; 424/178.1

(58) Field of Classification Search ........... 436/546, 436/172, 800; 435/968; 424/178.1
See application file for complete search history.

(56) References Cited

U.S. PATENT DOCUMENTS

| | | | |
|---|---|---|---|
| 3,887,379 A | 6/1975 | Clecak et al. ............ 95/115 R |
| 5,518,888 A | 5/1996 | Waldman ................ 435/7.23 |
| 5,563,132 A * | 10/1996 | Bodaness ................ 514/185 |
| 5,714,342 A | 2/1998 | Komoriya et al. ............ 435/23 |
| 6,004,536 A | 12/1999 | Leung et al. ................ 424/9.6 |
| 6,077,584 A | 6/2000 | Hurditch ................ 428/64.1 |
| 6,962,686 B2 * | 11/2005 | Kayyem et al. ............ 424/1.69 |
| 2003/0216795 A1 * | 11/2003 | Harth et al. ................ 607/88 |
| 2004/0151430 A1 | 8/2004 | Rajagopalan et al. | |

FOREIGN PATENT DOCUMENTS

| JP | 11174672 | 7/1999 |
|---|---|---|
| WO | WO02089858 | 11/2002 |
| WO | WO03003806 | 1/2003 |

(Continued)

OTHER PUBLICATIONS

PCT, *International Search Report*, PCT/US2004/032859, International filing date Oct. 7, 2004, 5 pg.

(Continued)

*Primary Examiner*—Long V. Le
*Assistant Examiner*—Shafiqul Haq
(74) *Attorney, Agent, or Firm*—Thompson Hine LLP

(57) ABSTRACT

The present invention discloses dye-azide derivatives and their bioconjugates for dual phototherapy of tumors and other lesions. The compounds of the present invention may contain either a mixture of Type 1 and Type 2 agents or a single entity that integrates both units in the same molecules. The compounds are designed to produce both Type 1 and Type 2 phototherapeutic effect at once using dual wavelength light source that will produce singlet oxygen and nitrene at the lesion of interest.

3 Claims, 2 Drawing Sheets

FOREIGN PATENT DOCUMENTS

| | | |
|---|---|---|
| WO | WO03004466 | 1/2003 |
| WO | WO03065888 | 8/2003 |

OTHER PUBLICATIONS

S. Achilefu, Ph.D. et al., *Novel Receptor-Targeted Fluorescent Contrast Agents for In Vivo Tumor Imaging*, Investigative Radiology, vol. 35, No. 8, 2000, 479-485.

Jerome Amaudrut et al., *The Thermal Sulfenate-Sulfoxide Rearrangement: A Radical Pair Mechanism*, J. Amer. Chem, Soc. , vol. 122, 2000, 3367-3374.

A. Andreoni et al., *Tumour photosensitization by chemotherapeutic drugs*, Biology, N3, 1993, 43-46.

Byron Ballou et al., *Tumor labelling in vivo using cyanine-conjugated monoclonal antibodies*, Cancer Immunology and Immunotherapy, vol. 41, 1995, 257-263.

M.D. Daniel et al., *A History of Photodynamic Therapy*, Aust. N.Z. J. Surg., vol. 61, 1991, 340-348.

T.J. Dougherty et al., *Photoradiation Therapy. II. Cure of Animal Tumors wiht Hematoporphyrin and Light*, Journal of the National Cancer Institute, vol. 55, No. 1, 1975, 115-121.

G. Freiherr, *the Light Stuff: Optical Imaging in Medical Diagnosis*, Medical Device & Diagnositc Industry Magazine, 1998, 40-46.

M.R. Hamblin et al., *On the mechanism of the tumour-localising effect in photodynamic therapy*, J. Photochem. Photobiol. B: Biol., vol. 23, 1994, 3-8.

J. C. Hebden et al., *Diagnostic imaging with light*, The British Journal of Radiology, vol. 70, 1997, S206-S214.

D.J. Hnatowich et al., *Radioactive Labeling of Antibody: A Simple and Efficient Method*, Science, vol. 220, 1983, 613-615.

G. Jori et al., *Second Generation Photosensitizers for the Photodynamic Therapy of Tumours*, Light in Biology and Medicine, vol. 2, R.H. Douglas et al. (Eds.), 1991, 253-266.

G. Jori, *Tumour photosensitizers: approaches to enhance the selectivity and efficiency of photodynamic therapy*, Journal of Photochemistry and Photobiology B: Biology, vol. 36, 1996, 87-93.

G. Jori, *Novel Therapeutic Modalitles Based on Photosensitized Processes*, Journal of Photochemistry and Photobiology B: Biology, No. 60, 1997, 12-18.

G. Jori, *Far-red-absorbing photosensitizers: their use in the photodynamic therapy of tumours*, J. Photochem. Photobiol. A: Chem. vol. 62, 1992, 371-378.

M. Korbelik, *Photosensitizers in photodynamic therapy*, Periodicum Biologorum, vol. 93, No. 4, 1991, 563-574.

K. Licha et al., *New contrast agents for optical imaging: acid-cleavable conjugates of cyanine dyes with biomedicals*, In Biomedical Imaging: Reporters, Dyes, and Instrumentation, D.J. Bomhop, C. Contag, and E.M. Servick-Muraca (Eds.), Proceedings of SPIE, vol. 3600, 1999, 29-35.

R.L. Lipson, M.D. et al., *Hematoporphyrin Derivative for Detection and Management of Cancer*, Cancer, vol. 20, No. 12, 1967, 2255-2257.

Y. Luo et al., *Rapid Initiation of Apoptosis by Photodynamic Therapy*, Photochemistry and Photobiology, vol. 63, No. 4, 1996, 528-534.

K. Matsumura, *1-Aminoacridine-4-carboxylic Acid*, Journal of the American Chemical Society, vol. 60, (1938) 591-593.

G.G. Miller et al., *Preclinical assessment of hypocrellin B and hypocrellin B derivatives as sensitizers for photodynamic therapy of cancer: progress update*, Photochemistry and Photobiology, vol. 65, No. 4, 1997, 714-722.

I. Ol'shevskaya, *Cyanine dyes from azidobenzothiazole and benzimidazole*, Chem. Ab. No. 1974:522571.

T. Parasassi et al., *Two-photon microscopy of aorta fibers shows proteolysis induced by LDL hydroperoxides*, Free Radical in Biology and Medicine, vol. 28, No. 11, 2000, 1589-1597.

D.J. Pasto et al., *Demonstration of the Synthetic Utility of the Generation of Alkoxy Radicals by the Proto-Induced, Homolytic Dissociation of Alkyl 4-Nitrobenzenesulfenates*, Tetrahedron Letters, vol. 35, No. 25, 1994, 4303-4306.

A. Pelegrin et al., *Photoimmunodiagnosis with antibody-fluorescein conjugates: in vitro and in vivo preclinical studies*, J. Cell Pharmacol, vol. 3, 1992, 141-145.

V. Pochinok et al., *Photochemistry of azide group containing dyes in solution*, Chem. Ab. No. 1984:439817.

W. G. Roberts et al., *Role of Neovasculature and Vascular Permeability on the Tumor Retention of Photodynamic Agents*, Cancer Research, vol. 52, 1992, 924-930.

G.I. Stables et al., *Photodynamic therapy*, Cancer Treatment Reviews, vol. 21, 1995, 311-323.

T. Takemura et al. , *Mechanism of Photodynamic Therapy: Exploration by Photophysiocochemical Study*, Frontiers of Photobiology, 1993, 503-506.

K.B. Trauner et al., *Photodynamic Synovectomy Using Benzoporphyrin Derivative in an Antigen-Induced Arthritis Model for Rheumatoid Arthritis.*, Photochemistry and Photobiology, vol. 67, No. 1, 1998, 133-139.

P.J. van Geel et al., *Photosensitizing Efficacy of MTHPC-PDT Compared to Photofrin-PDT in the RIFI Mouse Tumour and Normal Skin*, Int. J. Cancer, vol. 60, 1995, 388-394.

S. Sunthankar, et al., Reactive Disperse Dyes: Part I.—Reactivity Involving Nitrene Intermediate from Azido Group, Indian Journal of Chemistry, 1974 11(5): 503-504.

\* cited by examiner

METHODS AND COMPOSITIONS FOR DUAL PHOTOTHERAPY

CROSS-REFERENCE TO RELATED APPLICATIONS

This application is a Divisional of U.S. patent application Ser. No. 09/898,885, filed on Jul. 3, 2001, now abandoned, the disclosure of which is hereby incorporated by reference in its entirety.

FIELD OF THE INVENTION

The present invention relates generally to novel compounds useful for dual phototherapeutic procedures and particularly to phototherapeutic procedures using dye-azide compounds.

BACKGROUND OF THE INVENTION

The use of visible and near-infrared (NIR) light in clinical practice is growing rapidly. Compounds absorbing or emitting in the visible or NIR, or long-wavelength (UV-A, >350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is akin to radiotherapy, but it advantageously lacks the harmful radiotoxicity to critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek used eosin as a photosensitizer for treating skin cancer, lupus of the skin, and condylomata of female genitalia. Over the years, the combination of psoralens and ultraviolet A (low-energy) radiation has been used to treat a wide variety of dermatological diseases and manifestations including psoriasis, parapsoriasis, cutaneous T-cell lymphoma, eczema, vitiligo, areata, and neonatal bilirubinemia. Although the potential of cancer phototherapy has been recognized since the early 1900's, systematic studies to demonstrate safety and efficacy began only in 1967 with the treatment of breast carcinoma. In 1975, Dougherty et al. conclusively established that long-term cure is possible with photodynamic therapy (PDT). Currently, phototherapeutic methods are also being investigated for the treatment of some cardiovascular disorders such as atherosclerosis and vascular restenosis, for the treatment of rheumatoid arthritis, and for the treatment of some inflammatory diseases such as Chron's disease.

Phototherapeutic procedures require photosensitizers (i.e. chromophores) having high absorptivity. These compounds should preferably be chemically inert, and become activated only upon irradiation with light of an appropriate wavelength. Selective tissue injury can be induced with light when photosensitizers bind to the target tissues, either directly or through attachment to a bioactive carrier. Furthermore, if the photosensitizer is also a chemotherapeutic agent (e.g., anthracycline antitumor agents), then an enhanced therapeutic effect can be attained. The key requirements for the design of effective phototherapeutic agents are: (a) large molar extinction coefficients, (b) long triplet lifetimes, (c) high yields of singlet oxygen and/or other reactive intermediates, viz., free radicals, nitrenes, carbenes, or open-shell ionic species such as cabonium ions and the like, (d) efficient energy or electron transfer to cellular components, (e) low tendency to form aggregation in an aqueous milieu, (f) efficient and selective targeting of lesions, (g) rapid clearance from the blood and non-target tissues, (h) low systemic toxicity, and (i) lack of mutagenicity.

Photosensitizers operate via two distinct mechanisms, termed Types 1 and 2. The type 1 mechanism is shown in the following scheme:

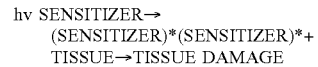

Type 1 mechanisms involve direct energy or electron transfer from the photosensitizer to the cellular components thereby causing cell death. Type 2 mechanisms involve two distinct steps, as shown in the following scheme:

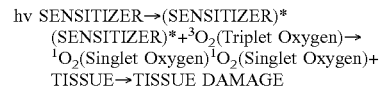

The biological basis of tissue injury brought about by tumor phototherapeutic agents has been the subject of intensive study. Various biochemical mechanisms for tissue damage have been postulated even though the type and number of photosensitizers employed in these studies are relatively small. These biochemical mechanisms are as follows: a) cancer cells upregulate the expression of low density lipoprotein (LDL) receptors, and photodynamic therapy (PDT) agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as photodynamic therapy (PDT) agents and operate via the Type 2 mechanism. For example, Photofrin II (a hematoporphyrin derivative) has been recently approved by the United States Food and Drug Administration for the treatment of bladder, esophageal, and late-stage lung cancers. However, Photofrin II has been shown to have several drawbacks: a low molar absorptivity ($\epsilon=3000$ M$^{-1}$), a low singlet oxygen quantum yield ($\phi=0.1$), chemical heterogeneity, aggregation, and prolonged cutaneous photosensitivity. Hence, there has been considerable effort in developing safer and more effective photosensitizers for PDT which exhibit improved light absorbance properties, better clearance, and decreased skin photosensitivity compared to Photofrin II. These include monomeric porphyrin derivatives, corrins, cyanines, phthalocyanines, phenothiazines, rhodamines, hypocrellins, and the like. However, these phototherapeutic agents also mainly operate via the Type 2 mechanism.

Surprisingly, there has not been much attention directed at developing Type 1 phototherapeutic agents, despite the fact that the Type 1 mechanism appears to be inherently more efficient than the Type 2 mechanism. First, unlike Type 2, Type 1 photosensitizers do not require oxygen for causing cellular injury. Second, the Type 1 mechanism involves two steps (photoexcitation and direct energy transfer), whereas the Type 2 mechanism involves three steps (photoexcitation, singlet oxygen generation, and energy transfer). Furthermore, certain tumors have hypoxic regions, which renders the Type 2 mechanism ineffective. However, in spite of the drawbacks associated with the Type 2 mechanism, only a small number of compounds have been developed that operate through the Type 1 mechanism, e.g. anthracyline antitumor agents.

Thus, there is a need to develop effective phototherapeutic agents. Phototherapeutic efficacy can be substantially improved if both Type 1 and Type 2 units are integrated into a single composition. This can be accomplished using three types of formulations: (a) homogeneous mixtures of Type 1 or Type 2 agents alone, (b) heterogeneous mixtures of Type 1 and Type 2 agents, or (c) a single molecular entity containing both Type 1 and Type 2 functionalities.

SUMMARY OF THE INVENTION

The present invention discloses novel compounds including organic azides for phototherapy of tumors and other lesions. More specifically, the present invention discloses compounds having the formula

wherein DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes. E is selected from the group consisting of somatostatin receptor binding molecules, ST receptor binding molecules, neurotensin receptor binding molecules, bombesin receptor binding molecules, cholecystekinin receptor binding molecules, steroid receptor binding molecules, and carbohydrate receptor binding molecules. L is selected from the group consisting of $-(CH_2)_a-$, $-(CH_2)_bCONR^1-$, $-N(R^2)CO(CH_2)_c-$, $-OCO(CH_2)_d-$, $-(CH_2)_eCO_2$, $-OCONH-$, $-OOO_2-$, $-HNCONH-$, $-HNCSNH-$, $-HNNHCO-$, $-OSO_2-$, $-NR^3(CH_2)_eCONR^4-$, $-CONR^5(CH_2)_fNR^6CO-$, and $-NR'CO(CH_2)_9CONR^8-$. X is either a single bond or is selected from the group consisting of $-(CH_2)_h-$, $-OOO-$, $-HNCO-$, $-(CH2)$; $CO-$, and $-(CH_2)_j OOO-$. $R^1$ to $R^8$ are independently selected from the group consisting of hydrogen, C1-C10 alkyl, $-OH$, C1-C10 polyhydroxyalkyl, C1-C10 alkoxyl, C1-C10 alkoxyalkyl, $-SO_3H$, $-(CH_2)_kCO_2H$, and $-(CH_2)$, $NR^9R^{10}$. $R^9$ and $R^{10}$ are independently selected from the group consisting of hydrogen, C1-C10 alkyl, C5-C10 aryl, and C1-C10 polyhydroxyalkyl. And a to 1 independently range from 0 to 10.

The present invention also discloses a method of performing a therapeutic procedure using the compounds of the present invention. An effective amount of organic azide photosensitizer having the formula

is administered to a subject. In this formula, DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes. E is a hydrogen atom or is selected from the group consisting of somatostatin receptor binding molecules, ST receptor binding molecules, neurotensin receptor binding molecules, bombesin receptor binding molecules, cholecystekinin receptor binding molecules, steroid receptor binding molecules, and carbohydrate receptor binding molecules. L is selected from the group consisting of $-(CH_2)_a-$, $-(CH_2)_bCONR^1-$, $-N(R^2)CO(CH_2)_c-$, $-OCO(CH_2)_d-$, $-(CH_2)_eCO_2$, $-OCONH-$, $-OOO_2-$, $-HNCONH-$, $-HNCSNH-$, $-HNNHCO-$, $-OSO_2-$, $-NR^3(CH_2)_eCONR^4-$, $-CONR^5(CH_2)_fNR^6CO-$, and $-NR'CO(CH_2)_g CONR^B-$. X is either a single bond or is selected from the group consisting of $-(CH_2)_h-$, $-OCO-$, $-HNCO-$, $-(CH2), CO-$, and $-(CH2), OOO-$. $R^1$ to $R^8$ are independently selected from the group consisting of hydrogen, C1-C10 alkyl, $-OH$, C1-C10 polyhydroxyalkyl, C1-C10 alkoxyl C1-C10 alkoxyalkyl, $-SO_3H$, $-(CH_2)_kCO_2H$, and $-(CH_2)$, $NR^9R^{10}$. $R^9$ and $R^{10}$ are independently selected from the group consisting of hydrogen, C1-C10 alkyl, C5-C10 aryl, and C1-C10 polyhydroxyalkyl. And a to 1 independently range from 0 to 10. Following administration, the photosensitizer is allowed to accumulate in target tissue which is exposed to a light of wavelength between 300 and 950 nm. This light has sufficient power and fluence rate to cause necrosis or apoptosis of the said target tissue.

In an alternative embodiment of the method, the compounds may be used to perform a phototherapeutic procedure including the following steps. A homogeneous photosensitizing mixture consisting of two or more Type 1 agents is prepared. This photosensitizing mixture is allowed to accumulate in target tissue which is exposed to a light of wavelength between 300 and 950 nm with sufficient power and fluence rate to cause necrosis or apoptosis of the target tissue.

In another alternative embodiment of the method, the compounds may be used to perform a phototherapeutic procedure including the following steps. A homogeneous photosensitizing mixture consisting of two or more Type 2 (PDT) agents is prepared. This photosensitizing mixture is allowed to accumulate in target tissue which is exposed to light of wavelength between 300 and 950 nm with sufficient power and fluence rate to cause necrosis or apoptosis of the target tissue.

In a further alternative embodiment of the method, the compounds may be used to perform a phototherapeutic procedure including the following steps. A heterogeneous photosensitizing mixture consisting of one or more Type 1 agents and one or more Type 2 agents is prepared. This photosensitizing mixture is allowed to accumulate in target tissue which is exposed to light of wavelength between 300 and 950 nm with sufficient power and fluence rate to cause necrosis or apoptosis of the target tissue.

These and other advantages and embodiments of the inventive compounds and methods will be apparent in view of the following Figures, description, and examples.

DETAILED DESCRIPTION OF THE INVENTION

Figure 1:
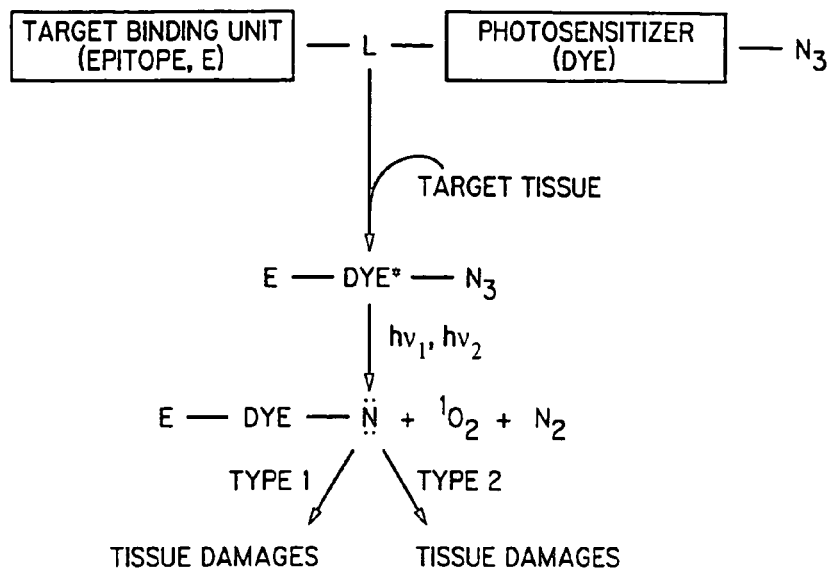
FIG. 1 is a schematic mechanism for activation of the inventive compounds.

The present invention discloses dye-azide derivatives and their bioconjugates for phototherapy of tumors and other lesions. The compounds have the general formula,

E-L-DYE-X—N$_3$ wherein DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, and the like; E is either a hydrogen atom or is selected from the group comprising antibodies, peptides, peptidomimetics, carbohydrates, glycomimetics, drugs, hormones, or nucleic acids; L is a linker unit selected from the group comprising —(CH$_2$)$_a$—, —(CH$_2$)$_b$CONR$^1$—, —N(R$^2$)CO(CH$_2$)$_c$—, —OCO(CH$_2$)$_d$—, —(CH$_2$)$_e$CO$_2$—, —OCONH—, —OCO$_2$—, —HNCONH—, —HNCSNH—, —HNNHCO—, —OSO$_2$—, —NR$^3$(CH$_2$)$_e$CONR$^4$—, —CONR$^5$(CH$_2$)$_f$NR$^6$CO—, and —NR$^7$CO(CH$_2$)$_g$CONR$^8$—; X is either a single bond or is selected from the group consisting of —(CH$_2$)$_h$—, —CO—, —OCO—, —HNCO—, —(CH$_2$)$_i$CO—, and —(CH$_2$)$_j$OCO—., R$^1$ to R$^8$ are independently selected from the group consisting of hydrogen, C1-C10 alkyl, —OH, C1-C10 polyhydroxyalkyl, C1-C10 alkoxyl, C1-C10 alkoxyalkyl, —SO$_3$H, —(CH$_2$)$_k$CO$_2$H, or —(CH$_2$)$_l$NR$^9$R$^{10}$; R$^9$ and R$^{10}$ are independently selected from the group consisting of hydrogen, C1-C10 alkyl, C5-C10 aryl, or C1-C10 polyhydroxyalkyl; and a to l independently range from 0 to 10.

In one embodiment, azides according to the present invention have the general formula 1 above wherein DYE is an aromatic or a heteroaromatic radical derived from the group consisting of cyanines, indocyanines, phthalocyanines, rhodamines, phenothiazines, fluoresceins, porphyrins, benzoporphyrins, and corrins; E is selected from the group consisting of somatostatin receptor binding molecules, (ST) receptor binding molecules, neurotensin receptor binding molecules, bombesin receptor binding molecules, cholecystekinin (CCK) receptor binding molecules, steroid receptor binding molecules, and carbohydrate receptor binding molecules; L is selected from the group consisting of —HNCO—, —CONR$^1$—, —HNCONH—, —HNCSNH—, —HNNHCO—, —(CH$_2$)$_a$CONR$^1$—, —CONR$^1$(CH$_2$)$_a$NR$^2$CO—, and —NR$^1$CO(CH$_2$)$_a$CONR$^2$—; R$^1$ and R$^2$ are independently selected from the group consisting of hydrogen, C1-C10 alkyl, C1-C10 polyhydroxyalkyl; and a, b, and c independently range from 0 to 6.

In an alternative embodiment, azides according to the present invention have the general formula 1 above wherein DYE is an aromatic or a heteroaromatic radical derived from the group consisting of cyanines, phthalocyanines, rhodamines, porphyrins, benzoporphyrins, and corrins; E is a selected from the group consisting of octreotide and octreotate peptides, ST receptor binding peptides, carcinoembryonic antigen antibody (anti-CEA), bombesin receptor binding peptide, neurotensin receptor binding peptide, cholecystekinin receptor binding peptide, and estrogen steroids; L is selected from the group consisting of —HNCO—, —CONR$^1$—, —HNCSNH—, —HNNHCO—, —(CH$_2$)$_a$CONR$^1$—, —CONR$^1$(CH$_2$)$_a$NR$^2$CO—, and R$^1$ and R$^2$ are independently selected from the group consisting of hydrogen, C1-C10 alkyl, C1-C5 polyhydroxyalkyl; and a, b, and c independently range from 0 to 6.

These compounds operate by a dual mechanism as shown in FIG. 1. N$_3$ is the azide moiety that produces nitrene upon photoactivation and DYE is an aromatic chromophore that undergoes photosensitization and produces singlet oxygen for PDT. Aliphatic azido compounds can also be used for phototherapy, but may require high-energy light for activation unless the azide moiety is attached to conjugated polyene system. L is a linker between the chromophore and the epitope. Epitope (E) is a particular region of the molecule that is recognized by, and binds to, the target site on the cell. An epitope is usually, but not always, associated with biomolecules, which includes hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of biomolecules include steroid hormones for the treatment of breast and prostate lesions, somatostatin, bombesin, and neurotensin receptor binding molecules for the treatment of neuroendocrine tumors, cholecystekinin (CCK) receptor binding molecules for the treatment of lung cancer, (ST) receptor and carcinoembryonic antigen (CEA) binding molecules for the treatment of colorectal cancer, dihyroxyindolecarboxylic acid and other melanin producing biosynthetic intermediates for melanoma, integrin receptor and atherosclerotic plaque binding molecules for the treatment of vascular diseases, and amyloid plaque binding molecules for the treatment of brain lesions. Biomolecules for use in the present invention may also include synthetic polymers. Examples of synthetic polymers include polyaminoacids, polyols, polyamines, polyacids, oligonucleotides, aborols, dendrimers, and aptamers. Coupling of diagnostic and radiotherapeutic agents to biomolecules can be accomplished by methods well known in the art, as disclosed in Hnatowich et al., *Radioactive Labeling of Antibody: A simple and efficient method. Science,* 1983, 220, 613-615; A. Pelegrin et al., *Photoimmunodiagnosis with antibody-fluorescein conjugates: in vitro and in vivo preclinical studies. Journal of Cellular Pharmacology,* 1992, 3, 141-145; and U.S. Pat. No. 5,714,342, each of which is expressly incorporated by reference herein in its entirety. Successful specific targeting of fluorescent dyes to tumors using antibodies and peptides for diagnostic imaging of tumors has been demonstrated by us and others, for example, in S. A. Achilefu et al., *Novel receptor-targeted fluorescent contrast agents for in vivo tumor imaging,* Investigative Radiology, 2000, 35(8), 479-485; B. Ballou et al., *Tumor labeling in vivo using cyanine-conjugated monoclonal antibodies. Cancer Immunology and Immunotherapy,* 1995, 41, 257-263; and K. Licha et al., *New contrast agents for optical imaging: acid-cleavable conjugates of cyanine dyes with biomolecules. In Biomedical Imaging: Reporters, Dyes, and Instrumentation,* D. J. Bornhop, C. Contag, and E. M. Sevick-Muraca (Eds.), Proceedings of SPIE, 1999, 3600, 29-35, each of which is expressly incorporated by reference herein in its entirety. Therefore, the inventive receptor-targeted phototherapeutic agents are expected to be effective in the treatment of various lesions.

In the present invention, dual phototherapeutic effect involving both Type 1 and Type 2 mechanisms can be accomplished by incorporating the reactive intermediate precursors into a conventional PDT dye and using a dual wavelength light source to effect the generation of reactive intermediates as well as the generation of singlet oxygen. In some cases it may be possible to activate both Type 1 and Type 2 mechanisms using same wavelength of light. Dyes containing azide group have been prepared previously, as in S. Sunthankar et al., *Reactive disperse dyes. 1. Reactivity involving nitrene intermediate from azido group. Indian Journal of Chemistry,* 1973, 11(5), 503-504, which is expressly incorporated by reference herein in its entirety.

In the process outlined in FIG. 1, the photoexcitation of the aromatic chromophore effects rapid intramolecular energy transfer to the azido group, resulting in bond rupture and production of nitrene and molecular nitrogen. The nitrogen that is released is in a vibrationally excited state, which may cause additional cellular injury.

For targeting purposes, external attachment of an epitope is used. If the aromatic azido compounds themselves preferentially accumulate in the target tissue, however, an additional binding group may not be needed. For example, if Ar is an anthracycline moiety, it will bind to cancer cells directly and would not require an epitope for targeting purposes.

Figure 2:
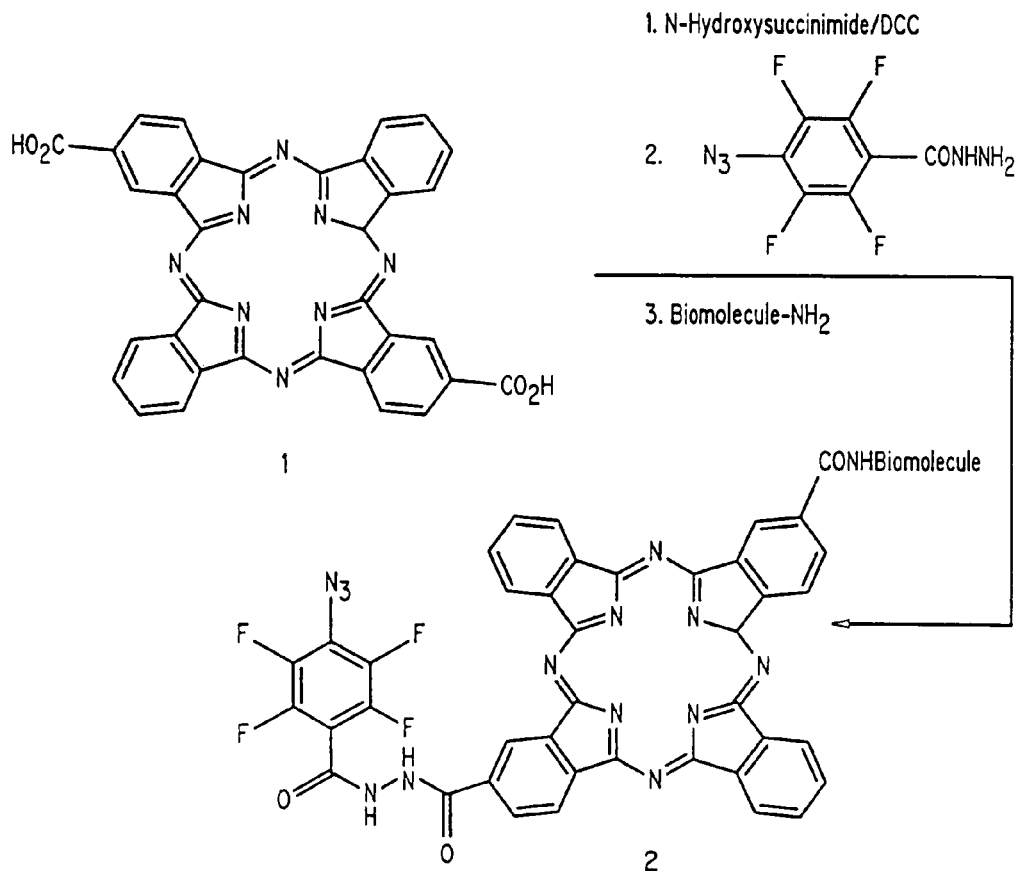
FIG. 2 is a schematic mechanism for the synthesis of a phthalocyanine derivative.
Figure 3:
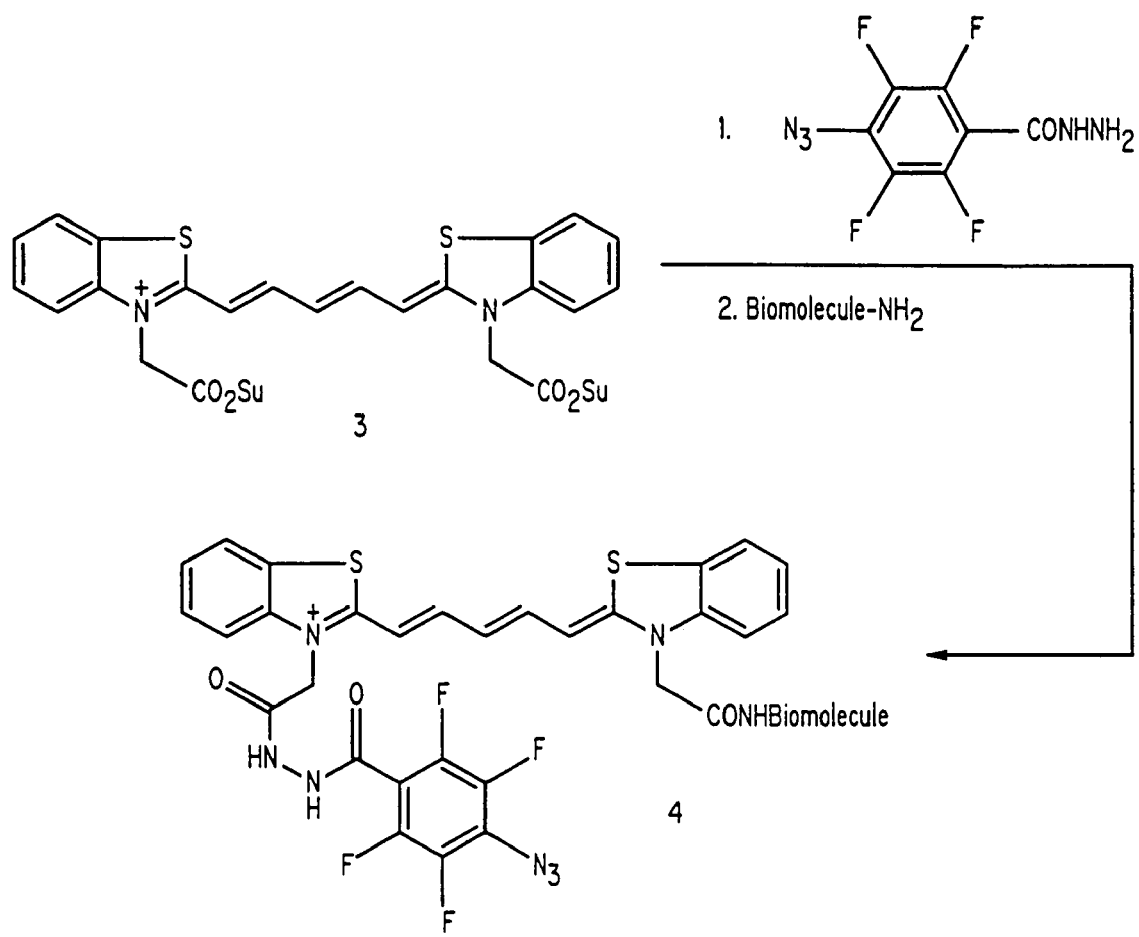
FIG. 3 is a schematic mechanism for the synthesis of a cyanine derivative.

The dye-azide derivatives of the present invention contain additional functionalities that can be used to attach various types of biomolecules, synthetic polymers, and organized aggregates for selective delivery to various organs or tissues of interest. The synthesis of typical dual phototherapeutic agents incorporating both Type 1 and Type 2 mechanisms based on phthalocyanine and cyanine derivatives are shown in FIGS. 2 and 3 respectively. Referring to FIG. 2, the diacid 1 can be prepared by the method analogous to phthalocyanine itself described previously in J. E. van Lier and J. D. Spikes, *The chemistry, photophysics, and photosensitizing properties of phthalocyanines, In Photosensitizing Compounds: Their Chemistry, Biology, and Clinical Use (Ciba Foundation Symposium* 146), G. Bock and S. Harnett (Eds.), J. Wiley & Sons, 1989, pp. 17-32, which is expressly incorporated by reference herein its entirety. The diacid 1 can be converted to the corresponding bis active ester in which one of the active esters can be condensed with an azide (by the Type 1 moiety) and the other active ester can be condensed with a biomolecule of interest to yield the phthalocyanine derivative 2. Referring to FIG. 3, the cyanine dye 3 is prepared by the alkylation of 2-methylbenzothiazole with N-succinimydyl bromoacetate followed by condensation with malonaldehyde tetramethyl acetal. One of the active esters in the cyanine dye 3 can be attached to a Type 1 moiety and the other ester can be attached to a biomolecule to give the dual phototherapeutic agent 4. Specifically, the biomolecules bind to colorectal, cervical, ovarian, lung, and neuroendocrine tumors, and include somatostatin, cholecystekinin, bombesin, neuroendrocrine, and ST receptor binding compounds. The other active ester can be conjugated to an aromatic or an aliphatic azides depending on the wavelength desired for excitation.

The novel compounds of the present invention may vary widely depending on the contemplated application. For tumors, the biomolecule is selected from the class of tumor markers including, but not limited to, somatostatin, bombesin, neurotensin, cholecystekinin, ST, estrogen, and progesterone receptor binding compounds. For vascular lesions, the biomolecule may be selected from the class of integrins, selecting, vascular endothelial growth factor, fibrins, tissue plasminogen activator, thrombin, LDL, HDL, Sialyl Lewis$^x$ and its mimics, and atherosclerotic plaque binding compounds.

Methods of performing therapeutic procedures with the inventive compound are also disclosed. An effective amount of the inventive compound in a pharmaceutically acceptable formulation is administered to a patient. For example, parenteral administration advantageously contains a sterile aqueous solution or suspension of the photosensitizer in a concentration ranging from about 1 nM to about 0.5 M. Preferred parenteral formulations have a concentration of 1 µM to 10 mM photosensitizer. Such solutions also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral formulations may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray. The dose of the photosensitizer may vary from 0.1 to 500 mg/kg body weight, preferably from 0.5 to 2 mg/kg body weight. The photosensitizer is allowed to accumulate in the region of interest, followed by illumination with the light of wavelength 300 to 1200 nm, preferably 350 to 850 nm, at the site of the lesion. If the lesion is on the skin surface, the photosensitizer can be directly illuminated; otherwise, endoscopic catheters equipped with a light source may be employed to achieve phototherapeutic effect. The intensity, power, duration of illumination, and the wavelength of the light may vary widely depending on the location and site of the lesions. The fluence rate is preferably, but not always, kept below 200 mW/cm$^2$ to minimize thermal effects. Appropriate power depends on the size, depth, and the pathology of the lesion. The inventive compounds have broad clinical utility which includes, but is not limited to, phototherapy of tumors, inflammatory processes, and impaired vasculature.

The inventive compounds can be formulated into diagnostic or therapeutic compounds for enteral, parenteral, topical, or cutaneous administration. Topical or cutaneous delivery of the photosensitizer may also include aerosol formulation, creams, gels, solutions, etc. The compounds are administered in doses effective to achieve the desired diagnostic or therapeutic effect. Such doses may vary widely depending upon the particular complex employed, the organs or tissues to be examined, the equipment employed in the clinical procedure, the efficacy of the treatment achieved, and the like. These compounds contain an effective amount of the phototherapeutic agent, along with conventional pharmaceutical carriers and excipients appropriate for the type of administration contemplated. These compounds may also include stabilizing agents and skin penetration enhancing agents.

The following example illustrates a specific embodiment of the invention pertaining to the preparation and properties of a typical bioconjugate derived from bombesin, a bioactive peptide; 4-azido-2,3,5,6-tetrafluorophenylbenzoyl hydrazide, a Type I chromophore; and carboxymethylcyanine dye, a PDT chromophore. The above-listed compounds are well known to those skilled in the art and general descriptions of the compounds and their synthesis are described in U.S. Pat. No. 6,180,085; Jori, G., *Far-red-absorbing photosensitizers: their use in the photodynamic therapy of tumours,* J. Photochem. Photobiol. A: Chem., 62, (1992), 371-378; Patonay, G. and M. Antoine, *Near-Infrared Fluorogenic Labels: New Approach to an Old Problem,*

Anal. Chem., 63:6, (1991) 321A-327A; and Jori, G. and E. Reddi, *Second Generation Photosensitizers for the Photodynamic Therapy of Tumours*, in *Light in Biology and Medicine*, Volume 2 (ed. R. H. Douglas et al.), Plenum Press, New York, (1991), 253-266, the disclosures of which are herein incorporated by reference in their entireties.

As would be apparent to skilled artisans, various changes and modifications are possible and are contemplated within the scope of the invention described. It should be understood that the embodiments of the present invention shown and described in the specification are only specific embodiments of the inventors, who are skilled in the art, and are not limiting in any way. Therefore, various changes, modifications or alterations to those embodiments may be made or resorted to without departing from the spirit of the invention and the scope of the following claims. For example, although the compounds of the present invention are primarily directed at therapy, most of the compounds containing polycyclic aromatic chromophores can also be used for optical diagnostic imaging purposes.

What is claimed is:

1. A method of performing a phototherapeutic procedure comprising:
    (a) administering a photosensitizing mixture to a target tissue in an animal, the photosensitizing mixture comprising organic azides having the formula E-L-DYE-X—$N_3$ wherein the organic azides function through both type 1 and type 2 mechanisms and where
    DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, and indolenium dyes;
    E is a hydrogen atom or is selected from the group consisting of somatostatin receptor binding molecules, ST receptor binding molecules, neurotensin receptor binding molecules, bombesin receptor binding molecules, cholecystekinin receptor binding molecules, steroid receptor binding molecules, and carbohydrate receptor binding molecules;
    L is selected from the group consisting of —$(CH_2)_a$—, —$(CH_2)_b CONR^1$—, —$N(R^2)CO(CH_2)_o$—, —OCO$(CH_2)_d$—, —$(CH_2)_e CO_2$—, —OCONH—, —$OCO_2$—, —HNCONH—, —HNCSNH—, —HNNHCO—, —$OSO_2$—, —$NR^3(CH_2)_e CONR^4$—, —$CONR^5(CH_2)_f NR^6 CO$—, and —$NR^7 CO(CH_2)_g CONR^8$—;
    X is either a single bond or is selected from the group consisting of —$(CH_2)_h$—, —OCO—, —HNCO—, —$(CH_2)_i CO$—, and —$(CH_2)_j OCO$—;
    $R^1$ to $R^8$ are independently selected from the group consisting of hydrogen, C1-C10 alkyl, —OH, C1-C10 polyhydroxyalkyl, C1-C10 alkoxyl, C1-C10 alkoxyalkyl, —$SO_3H$, —$(CH_2)_k CO_2H$, and —$(CH_2)_l NR^9 R^{10}$;
    $R^9$ and $R^{10}$ are independently selected from the group consisting of hydrogen, C1-C10 alkyl, C5-C10 aryl, and C1-C10 polyhydroxyalkyl; and
    a to l independently range from 0 to 10; and
    (b) exposing the target tissues to light of wavelength between 300 and 950 nm with sufficient power and fluence rate to enable the organic azides to cause necrosis or apoptosis of the target tissue.

2. The method of claim 1 wherein said photosensitizing mixture comprises azides, phthalocyanines and porphyrins.

3. The method of claim 2 further comprising the step of allowing the photosensitizing mixture to accumulate in the target tissue before exposure to light.

* * * * *

UNITED STATES PATENT AND TRADEMARK OFFICE
CERTIFICATE OF CORRECTION

| | |
|---|---|
| PATENT NO. | : 7,303,926 B2 |
| APPLICATION NO. | : 10/776840 |
| DATED | : December 4, 2007 |
| INVENTOR(S) | : Raghavan Rajagopalan et al. |

Page 1 of 1

It is certified that error appears in the above-identified patent and that said Letters Patent is hereby corrected as shown below:

COLUMN 10
Line 7, "$(CH_2)_o$" should read --$(CH_2)_c$--.

Signed and Sealed this

Thirteenth Day of May, 2008

JON W. DUDAS
*Director of the United States Patent and Trademark Office*